United States Patent [19]

Wanderman et al.

[11] Patent Number: 5,511,561
[45] Date of Patent: Apr. 30, 1996

[54] GAIT CYCLE FORCE MONITOR

[76] Inventors: Steven M. Wanderman, 107 Southern Trace Ct., Peachtree City, Ga. 30269; Glenn F. Bader, 78 Oronoque Trail, Shelton, Conn. 06484

[21] Appl. No.: 976,549

[22] Filed: Nov. 16, 1992

[51] Int. Cl.$^6$ ............................................. A61B 5/103
[52] U.S. Cl. ............................................. 128/779; 73/172
[58] Field of Search ............................ 128/774, 779, 128/903–904; 33/3 A; 340/573, 626; 73/172, 715, 723–731

[56] References Cited

U.S. PATENT DOCUMENTS

| | | | |
|---|---|---|---|
| 3,791,375 | 2/1974 | Pfeiffer. | |
| 3,974,491 | 8/1976 | Sipe | 128/779 X |
| 4,195,643 | 4/1980 | Pratt, Jr. | 128/779 |
| 4,444,205 | 4/1984 | Jackson | 128/782 |
| 4,503,705 | 3/1985 | Polchaninoff | 128/779 |
| 4,647,918 | 3/1987 | Goforth | 340/573 |
| 4,649,933 | 3/1987 | Jackson | 128/774 |
| 4,649,934 | 3/1987 | Fraser et al. | 128/782 |
| 4,745,930 | 5/1988 | Confer | 128/779 |
| 4,754,763 | 7/1988 | Doemland | 128/739 |
| 4,858,620 | 8/1989 | Sugarman et al. | 128/774 |
| 4,979,516 | 12/1990 | Abraham, II | 128/777 |
| 5,050,618 | 9/1991 | Larsen | 128/774 |
| 5,107,854 | 4/1992 | Knotts et al. | 128/779 |
| 5,253,654 | 10/1993 | Thomas et al. | 128/779 |
| 5,269,081 | 12/1993 | Gray | 128/779 X |

FOREIGN PATENT DOCUMENTS

| | | | |
|---|---|---|---|
| 0001574 | 3/1987 | WIPO | 128/779 |

OTHER PUBLICATIONS

"Engineering for the Human Body" Soma, vol. 3, No. 3, 1989, pp. 1–6.
"A Pressure Mapping System for Gait Analysis"; *Sensors*; May 1991—pp. 21–25.
Research and Developments "Grasp Force Sensor Gives Medicine a Hand" Stephanie vL Henkel.
Product Spotlight—Relays, Switches & Sensors.

*Primary Examiner*—Angela D. Sikes

[57] ABSTRACT

A foot-pad monitor to detect the amount of force translated though a patient's heel in each gait cycle is described. The foot-pad has a tactile force sensor, means to translate a force applied to the sensor to a voltage, a comparator circuit and an annunciator. The comparator, which can be analog or micro-processor controlled, has a set point and an amplifier that is activated when the voltage from the sensor exceeds the set point. The piezo-electric annunciator is driven by the amplifier to warn the patient that excessive force is being translated through the heel. In the analog embodiment the reference voltage can be varied by adjusting linearly variable pots. Also described is a remote unit to set the set point limit in the micro-processor controlled embodiment.

9 Claims, 5 Drawing Sheets

GAIT CYCLE FORCE MONITOR

FIELD OF THE INVENTION

The present invention relates to treatment of orthopedic conditions of the lower extremities. More particularly it relates to measurement and monitoring of forces placed on a foot.

BACKGROUND OF THE INVENTION

Historically, experts believed that patients with healing bones of the lower extremities (following surgery, reduction, or replacement) should refrain from placing any compressive force on the extremity, as happens when walking, until the bone had begun to heal. Today, orthopedists and researchers have learned that placing some force on the limb will generate piezoelectric currents which stimulate bone healing. Excessive force, however, may result in delayed union, nonunion or possibly malunion of the bone. Thus for each fracture type (spiral, oblique, transverse and so on) and location of fracture an optimal and measurable range of force should be placed across the fracture to maximize healing potential. The peak force needs to be monitored in each gait cycle to be certain that it does not exceed a maximum limit prescribed by the physician. Total force translated through the heel should be measured regardless of whether the patient first strikes the heel or the toe.

When physicians provide written orders to physical therapists regarding ambulation training, they typically instruct "partial weight bearing status". These instruction are vague with the result that some patients may place inadequate force on the limb while others apply excessive force on the limb. Healing may be delayed when inadequate force is applied. When excessive force is transmitted the healing properties may also be adversely affected resulting in further disability and the need for extended and costly care. Additional surgeries and lengthy immobilization, along with their associated risks, represent a few of the potential complications. With the development of porous coated joint replacements, the need to monitor weight bearing is also critical to optimize the potential for bone ingrowth into the porous interface.

A device to warn of excessive force applied to a lower extremity is described in U.S. Pat. No. 3,791,375 to Pfeiffer. That patent shows two sensors for positioning beneath a patient's foot connected to a sensing/signal unit to be secured to the patient's ankle. Each sensor is comprised of two plates spaced apart by a fluid. The sensor requires a resilient spacer to keep the two plates apart at zero force, but no specific materials are suggested. Upon application of a force, the resilient spacer is deformed allowing the two plates to come closer together displacing some of the fluid between them. The fluid displaced travels to bellows within the signal unit which expand. When the bellows expand enough, a switch arm is engaged and pushed into its opposing contact. An audible alarm sounds when the electrical circuit is completed. The patent does not specify any particular type of audible alarm. The patent describes adjustment of the space between the switch arm and the opposing contact so that the force required to bring the two parts together can be varied. However, this method of establishing and varying the set limit is imprecise as the resistance of the spring would be expected to decrease after extended use. Calibration against an external reference is required for precise setting of the force limit. Once the set limit has been set repeated calibration and adjustment would be required to maintain the desired limit. Of necessity the sensor and sensing/signal unit are connected. Sensors that measure force by detecting deformation of a resilient spacer suffer from the need for costly, complex mechanisms which in use over a lengthy period would be expected to break.

Pfeiffer also describes an electro-mechanical embodiment which like the hydraulic embodiment dependents on variation in the distance between two deformable plates as an indication of force. In that embodiment the top plate of the sensor has a contact mounted on its lower surface. The bottom plate has a switch arm mounted on its upper surface. The distance between the switch arm and the contact at zero force is set with a set screw. Upon deformation of the upper plate the contact and switch arm meet to complete an electric circuit which actuates the signal.

A resistance sensor offered by Tekscan, Inc. (Boston, Mass.) is described in SENSORS, pp 21–25, May 1991. This monitor is a force mapping system for gait analysis. The force sensor comprises a grid of conductive ink. The rows are separated from the columns by a coat of a force sensitive resistive ink having resistance inversely proportional to force. The force distribution over the sensor's surface is determined by scanning the grid and measuring resistance at each intersection. The system includes a signal detecting/ transmission unit designed as an ankle pack having hardware to drive and multiplex the circuit, amplifiers and multiplexors to receive and transmit the output current, analog to digital converter and a parallel to serial converter. The analog to digital convertor in the signal detection unit requires substantial volume, uses significant power and is costly. Finally, the system includes a signal measurement/ analysis circuit where the data stream from the ankle pack is reconverted to analog and analyzed. The system's software provides real-time two and three dimensional views of force patterns applied to the sensor. For calibrated measurements the foot pad must be calibrated in a calibration frame.

A capacitance sensor under development at Case Western Reserve University to measure grasp force of a hand is briefly described in SENSORS, p. ,19__. This sensor comprises chromium and gold rows and columns pattern coated onto polyimide substrates. The pattern coated films are separated by a layer of silicone which forms a compliant dielectric layer. The circuitry to detect, transmit and analyze and report the force applied to the sensor are not described.

A need exists, therefore, for a simple effective monitor to determine if a force applied by a patient to a limb exceeds a value set for the patient and to warn the patient when the predetermined upper limit is exceeded. Today no such device exists.

SUMMARY OF THE INVENTION

The monitor of the present invention comprises a single foot-pad unit for placement below a patient's foot that includes a tactile force sensor, means to translate a force applied to the tactile force sensor to a voltage, a comparator circuit having a set point and an amplifier that is activated when the voltage from the force sensor is greater than the set point, a piezo-electric annunciator and a power source. The functional components of the food-pad are encased in a protecting material.

The set point may be preset, or the comparator circuit may comprise means to vary the set point. The tactile force sensor may be a capacitance sensor in which case the means to translate a force applied to the sensor to a voltage is an AC bridge. Alternatively, the tactile force sensor may be a resistance sensor in which case the means to translate a force applied to the tactile force sensor is a linearized bridge.

In one embodiment the comparator circuit is an analog voltage comparator and the set point is the voltage of a reference circuit. A ratio metric voltage comparator circuit uses little power and occupies a small volume. Surprisingly, compensation for any non-linearity in the sensor can be made by selection of an appropriate voltage for the reference circuit and inclusion of a linearizing amplifier in the circuitry for the tactile force sensor.

In this embodiment the set point can be set precisely without need for external calibration by defining the resistance in the reference circuit of the comparator. The resistance of the reference circuit can conveniently be changed by replacing the resistor with a different resistor. Alternatively, the comparator may include a linearly variable pot having a dial so that the voltage of the reference circuit is set by applying to the sensor a force equal to the desired set limit and adjusting the dial. In this embodiment the dial extends to an external surface of the encasing material to be accessible to a user.

To eliminate the need for calibration by the prescribing physician or physical therapist, the linearly variable pot can be equipped with a calibration cover surrounding the dial that is marked to show the position required of the dial to achieve specific set limits, e.g. increments of five pounds.

To achieve a very broad dynamic range of set points and the ability to precisely set a set point, the reference circuit can be equipped with a plurality of linearly adjustable pots. For example, the circuit may have a first pot having a resistance range of 0 to 120 k ohms for gross adjustments in increments of 5 or 10 pounds and a second pot with a resistance range of 0 to 10 k ohms for fine adjustment in increments of 1 pound. First and second calibration covers indicate the positions required of the dials for each pot to achieve certain set points.

In another alternative, the comparator may comprise an analog-to-digital converter and a micro-processor programmed to drive the annunciator when a preset set point is exceeded. In this embodiment the set point is set by programming the processor with the desired limit. The set point may be varied by using a remote control to set a new limit. Alternatively, the sensor can be equipped with an switch on its exposed surface that is used to vary the set point.

In both the analog ratio metric voltage comparator and the analog-to-digital convertor micro-processor comparator embodiments, the monitor may be equipped with a security lock, a keyed switch or a password protected program, to preclude inadvertent tampering with the limit by the patient.

The annunciator is a piezo-electric speaker which is efficient, thin and cost effective. By virtue of its high impedance, a piezo-electric speaker may be driven by directly by the comparator. A single speaker is suitable for the full dynamic range of force limits desired (for example from 5 to 500 pounds in 5 pound increments) because the sensor measuring device is set to activate the speaker circuit with a defined voltage. Piezo-electric speakers also have a suitable frequency response.

Conveniently the sensor and the sensor measuring device may be combined in a single integrated circuit. The annunciator is a separate device connected to the flex circuit material. This design enables extremely low cost production so that the sensor is a single use device.

In an alternative embodiment the monitor further comprises a remote unit to receive the output of the annunciator for storage or further processing, for example for conversion into an audible signal or into a form suitable for visual output. In this embodiment when the remote unit is included, the output of the piezo-electric speaker may be electromagnetic energy requiring hard wire connection to the foot pad sensor or preferably is ultrasound energy. To avoid interference, the output signal may be encoded by the comparator circuit. The receiver strips the carrier frequency and upon recognition of the encoded pattern activates a signal system, e.g. a light circuit or a printer. Alternatively, the cycle may be stored as a function of time for cycle counting summation.

Alternatively, the comparator and annunciator circuitry may be designed to output both an audible signal and an encoded ultrasound signal. This can be achieved by driving the annunciator at a frequency in the audible range for a discrete interval followed by an interval when the speaker transmits an encoded ultrasound signal that is received and decoded by the remote unit. In this embodiment, hearing impaired patients are provided with a remote unit which receives the encoded ultrasound signal, strips the carrier frequency and upon recognition of the encoded pattern activates a light signal circuit (e.g. a light emitting diode circuit). Hearing patients are warned by the audible signal and do not need the remote receiver unit.

The foot pad sensor assembly can be conveniently secured to a patient's foot by securing it to a disposable slipper. Any one of many fastening systems may be used. A particularly convenient system requires attaching one side of a loop and hook fastening system, e.g. a Velcro® brand fastening system, to the upper surface of the transducer. Then the other side of the loop and hook fastening system is secured to the lower surface of the disposable slipper.

Alternatively, when the patient is to wear a foot cast, the sensor can be wrapped into the cast as it is applied. When affixed in this fashion, the switch or dial(s) used to set the force limit should remain exposed if the physician intends to vary the force limit as the patient's condition improves.

DETAILED DESCRIPTION OF THE INVENTION

Figure 1:
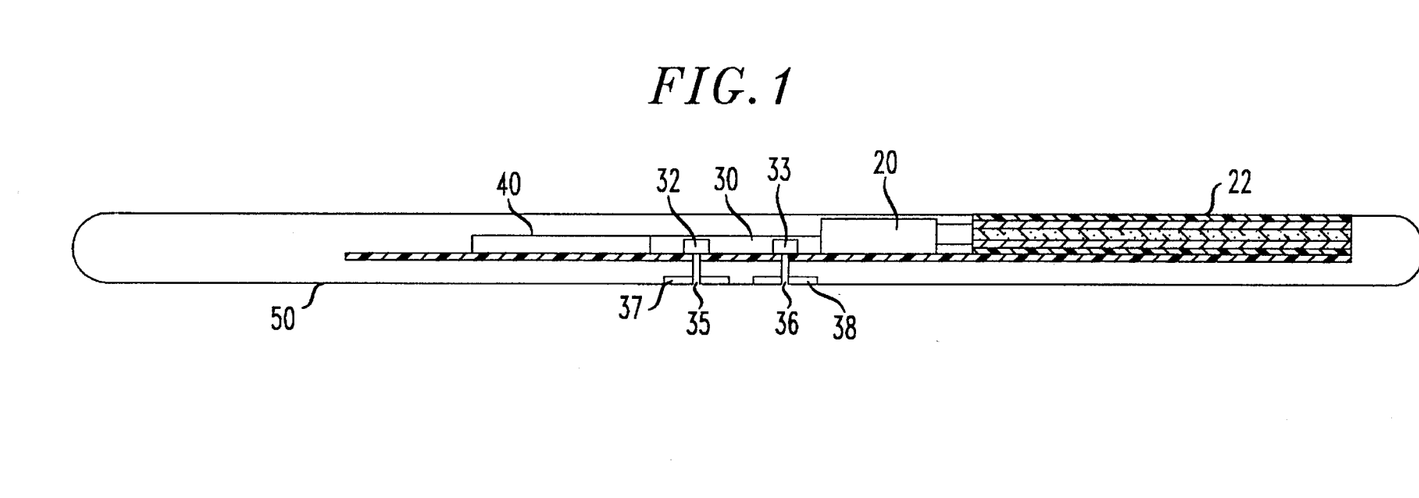
FIG. 1 shows a section view of the foot pad monitor of the present invention.

FIG. 1 shows the foot-pad unit of the present invention. The unit comprises power source 10, linearized bridge 20 including tactile load sensor 22, comparator 30 and annunciator 40. The functional components are conveniently mounted on a flex circuit support. Other materials can be selected for the support provided that they are conformable and durable. To protect the sensor from moisture and extreme temperature variations and to cushion the components from the shear, torsional and compression forces applied in use, all the components are assembled in a housing 50 made of silicone rubber. The tactile load sensor is mounted in area that will be placed under a patient's heel in use and connected by leads 224 to the linearized bridge. Dials 35 and 36 to vary the set point limit in the analog embodiment of the sensor extend from pots 32 and 33 to the exposed surface of the unit where calibration covers 37 and 38 indicate set points in suitable increments.

Figure 2:
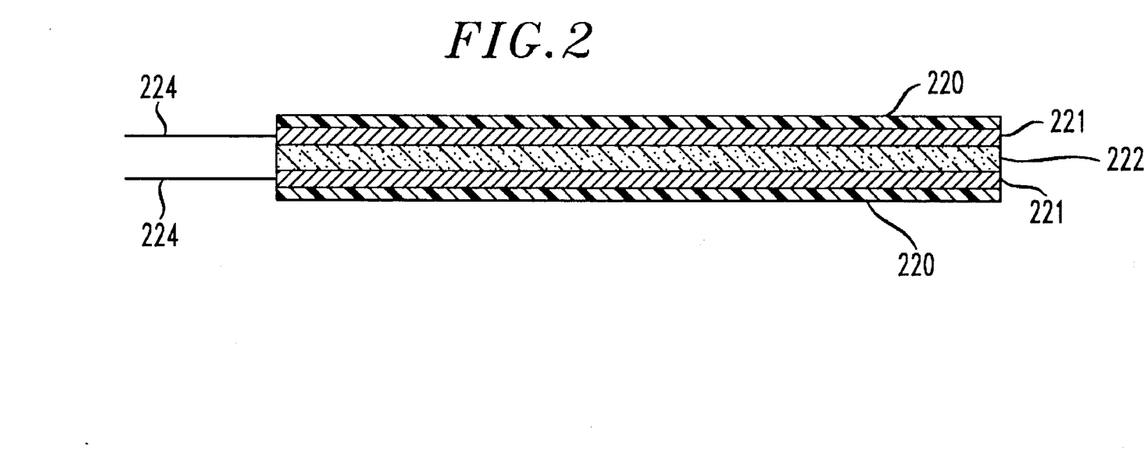
FIG. 2 shows a section view of a flexible sensor for use in the footpad monitor.

The construction of tactile sensor 22 is shown in FIG. 2. The sensor comprises two dielectric film supports 220 which are each coated on one surface with a conductive layer 221. The film supports are positioned with their conductive layers facing each other. Sandwiched in between the layers 221 of conductive ink is a compressible semi-conductor layer 222. The support 220 is conveniently made of polyester film, e.g. "Scotchpar" brand polyester film available from Minnesota Mining and Manufacturing Company, St. Paul, Minn. The conductive layer 221 is conveniently a coating of conductive ink, e.g. #5005 silver composition ink available from E. I. du Pont De Nemours, Co. Wilmington, Del. Suitable metalized polyester films are readily available. The semi-conductor layer 222 is comprised of conductive particles (e.g. silver or graphite) suspended in a polymeric binder. Suitable materials are described in U.S. Pat. No. 4,856,993 to Maness et al. The entire composite is commercially available from Tekscan, Inc., Boston, Mass. (a F-Scan™ unit) or from Dynaforce, Chicago, Ill. (a generic unit).

Figure 3:
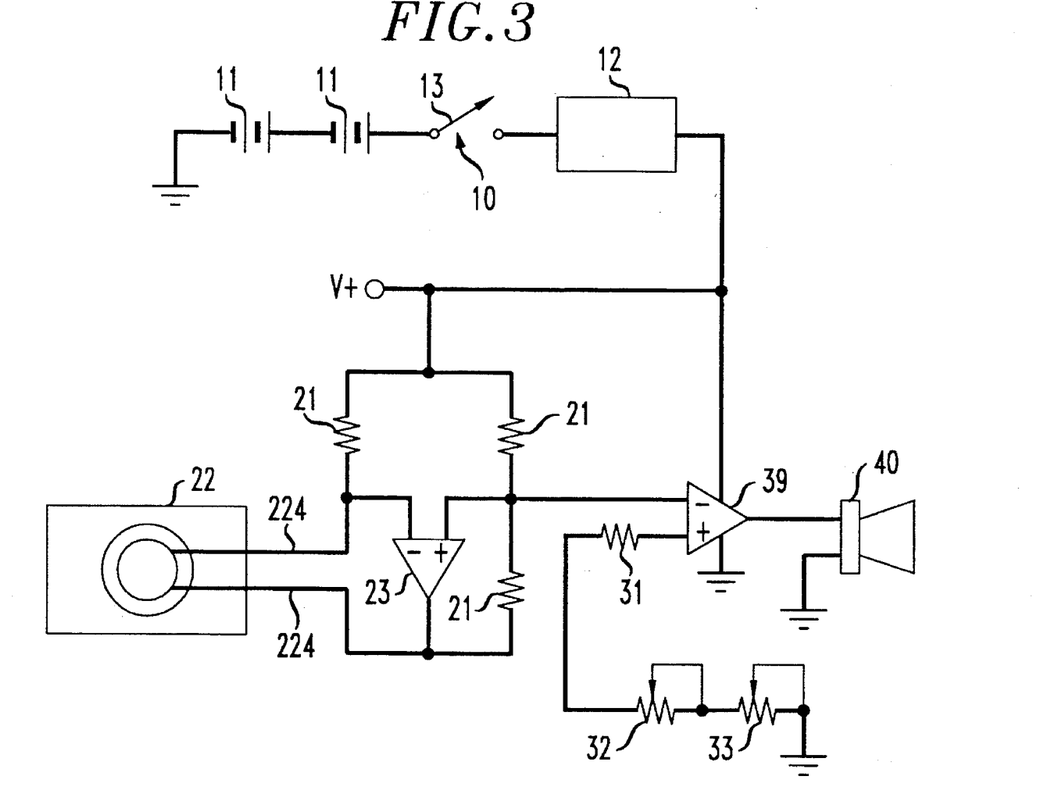
FIG. 3 is a detailed circuit diagram of a foot pad unit having a ratio voltage comparator and annunciator circuit.

FIG. 3 shows a detailed circuit diagram of a ratio metric voltage comparator and annunciator circuit for use as the sensor measuring device. The circuit comprises a power source 10, a linearized bridge 20, a comparator circuit 30 and piezo-electric annunciator 40.

The power source 10 is two batteries 11 of 1½ V each boosted to 12 volts by a power booster chip 12. This configuration gives a small power source with approximately 6 months useful life. The power source circuit may optionally include a spring loaded switch 13 that is biased to open the power source circuit at zero load and to close the circuit upon application of a minimum load, e.g. 1 pound. Also a low voltage alarm could be included if desired. Alternatively, the batteries can be tested before installation and at regular intervals thereafter.

The linearized bridge 20 has three resistors 21 of fixed resistance e.g. 120 k ohms, and a tactile sensor 22 with resistance varying as a function of force applied to the sensor. In the absence of any force applied the resistance of the tactile sensor 22 is equal to that of the three fixed resistors, e.g. 120 k ohms. Linearizing amplifier 23 compensates for any non-linearity in the change in resistance of the tactile sensor as a function of force applied. The linearizing amplifier is selected to have low offset voltage, for example less than 10 μv and low current, e.g. less than 10 na. The amplifier's drift should also be low, for e.g. 0.2 μv/degree C., because these three parameters, voltage, current and drift are amplified by the comparator.

The reference circuit of voltage comparator 30 is conveniently comprised of a fixed resistor 31 and a variable resistor. The value of the fixed resistor should be set no greater than required for the minimum load on the sensor, e.g. 5 lbs. With a 12 volt power source, a tactile sensor constructed as described above, and 120 k ohm resistors in the bridge, the fixed resistor should have a resistance of 120 k ohms. As shown, the variable resistor comprises linearly variable pots 32 and 33. To achieve a large dynamic range, e.g. 5 to 500 lbs., and the ability to precisely set the set point, e.g. in increments of 1 lb., linearly adjustable pot 32 has a broad dynamic range of 0 ohms to 100 k ohms. Linearly adjustable pot resistor 33 is chosen to have a smaller dynamic range, e.g. 0 ohms to 10 k ohms, to permit fine adjustments.

Figure 11:
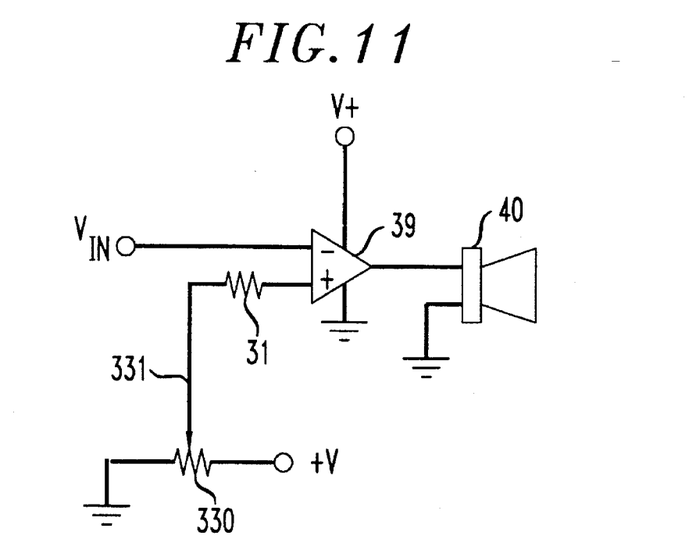
FIG. 11 shows an alternative ratio voltage comparator circuit.

An alternative embodiment for the comparator circuit is shown in FIG. 11. In this embodiment, the reference circuit of the comparator 30 is comprised of a 100 ohm current limiting fixed resistor 330 connected to wiper 331 of 10 k-10 turn pot 330. The range of the pot is between the power source and ground.

In operation, when the voltage put out by the bridge 10 exceeds the voltage of the reference circuit, the comparator amplifier 39 gives out a voltage to the annunciator 40. Increasing the resistance of the pot will increase the reference voltage which in turn increases the amount of force that can be applied to the tactile sensor 22 before the voltage from the bridge exceeds the reference voltage.

A calibration cover may be added to each of the pots shown in FIG. 3 or to the single pot shown in FIG. 11. In the dual pot embodiment, calibration cover 37 is marked to show gross increments, e.g. increments of 10 pounds, while calibration cover 38 is marked to show fine increments, e.g. increments of 1 pound. In the single pot embodiment, the calibration cover can be marked to show increments of 5 pounds.

In the simplest embodiment of the present invention, the annunciator is a speaker, e.g. a piezo electric speaker, oscillating at a rate in the audible range, e.g. 2000 hz. If a remote signalling unit is desired a the annunciator can be selected to put out an encoded ultrasound signal that is received by remote unit which in turn gives off a signal, e.g. a flashing light or shrill alarm. Where a audible alarm in the sensor and a remote visual alarm are desired, a second annunciator can be added. In this way the first annunciator oscillates in the audible range and the second annunciator produces an encoded ultrasound signal to activate an liquid crystal display in a remote unit.

Figure 4:
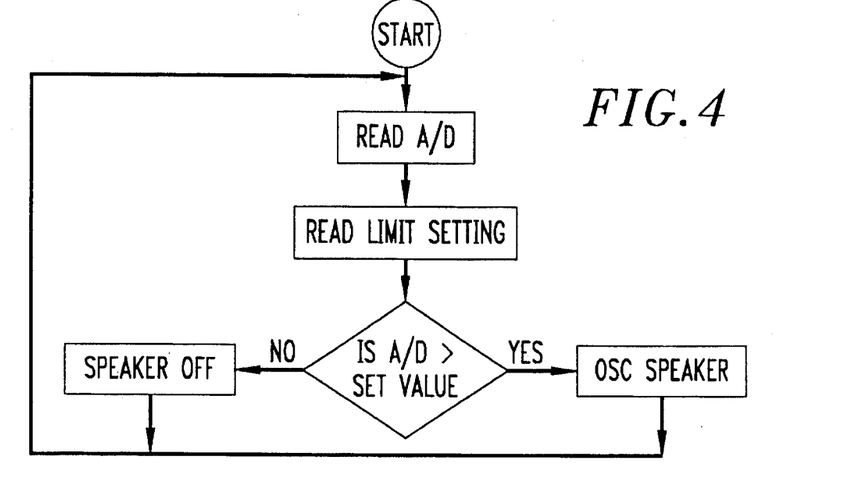
FIG. 4 is a flow chart showing a micro-processor controlled comparator routine.

A micro-processor controlled comparator routine is shown in FIG. 4. In this embodiment the sensor comprises a linearized bridge as described above, a micro-processor controlled comparator and an annunciator. The output of the linearized bridge is converted to digital and compared to the set point programmed into the micro-processor. If the output from the bridge is greater than the value programmed as the set point, the annunciator speaker is oscillated. If the output of the bridge is lower than the value programmed as the set point the speaker remains off. The comparator process is repeated at discrete intervals.

Figure 5:
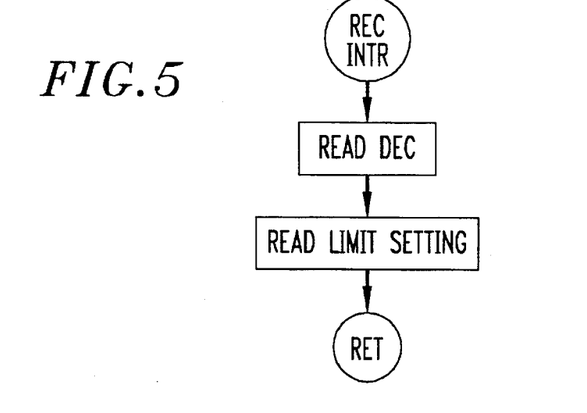
FIG. 5 is a flow chart showing a write routine to change the reference voltage of the comparator.

FIG. 5 shows a routine to change the set point setting. In this routine, an ultrasound interrupt signal is transmitted from a remote unit, received by an ultrasonic decoder in the footpad unit, converted to digital and decoded by the microprocessor. The interrupt signal instructs the processor to stop the comparator routine and receive and decode a new set point value. The new set point value overwrites the preexisting set point value, a confirmation signal is sent to the remote unit, and the comparator routine is resumed.

Figure 6:
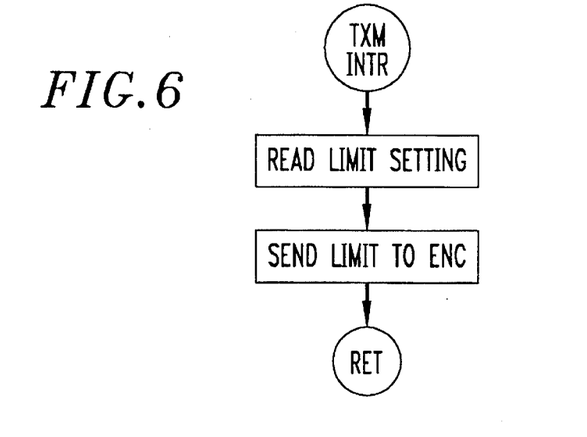
FIG. 6 is a flow chart showing a read routine to allow a user to determine the value of a set point programmed into the foot-pad.

FIG. 6 shows a routine to instruct the foot-pad to read out its existing set point value. An ultrasound or infrared interrogation signal is transmitted by a remote unit. The signal is received by the sensor and decoded. The signal instructs the processor to read its existing set point value, encode it and transmit the encoded value to the remote unit.

Figure 7:
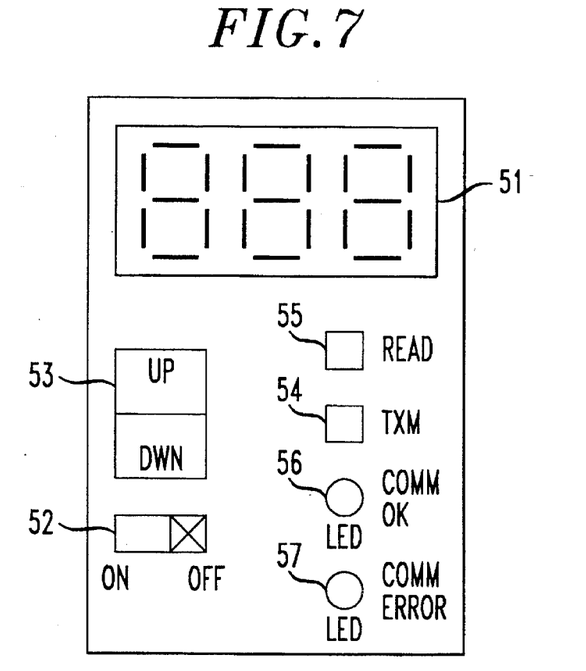
FIG. 7 is a top plan view showing the lay out of a remote unit to interact with the micro-processor of the foot-pad.
Figure 8:
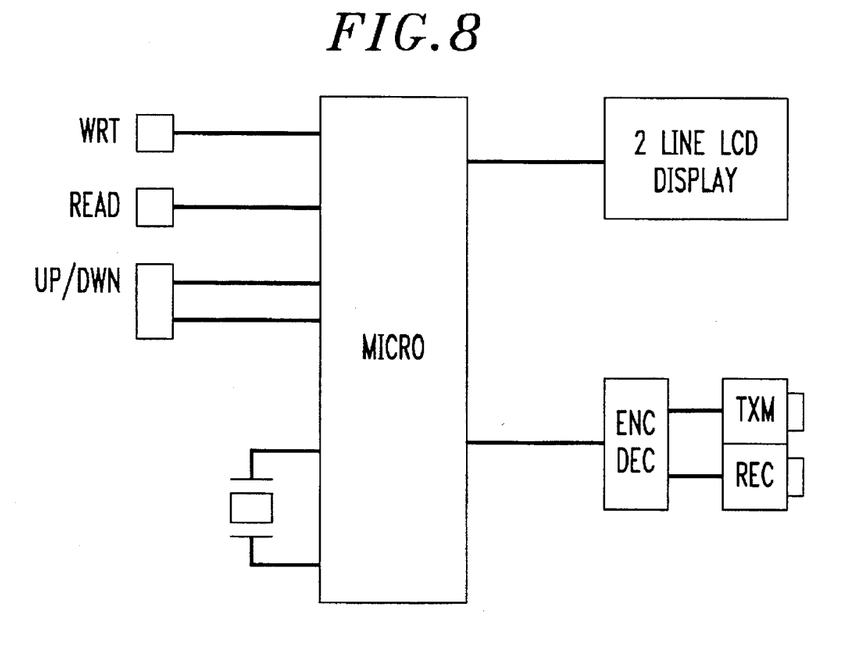
FIG. 8 is a circuit diagram for the remote unit shown in FIG. 7.

FIG. 7 shows a layout of a remote unit for setting and interrogating the sensor unit. FIG. 8 shows the circuitry for the remote unit of FIG. 7. The remote unit 50 comprises a liquid crystal display 51, an on/off switch 52, and a rocker 53 switch to increase or decrease the value shown in the liquid crystal display. A transmit button 54 is used to activate a write routine to reset the set point value in the sensor with the value currently displayed in the liquid crystal display. A read button 55 activates a read routine to inquire of the sensor unit the value of the current set point. Indicator lights 56 and 57 serve either to confirm completion of a successful communication or to indicate a communication error as the case may be.

Figure 9:
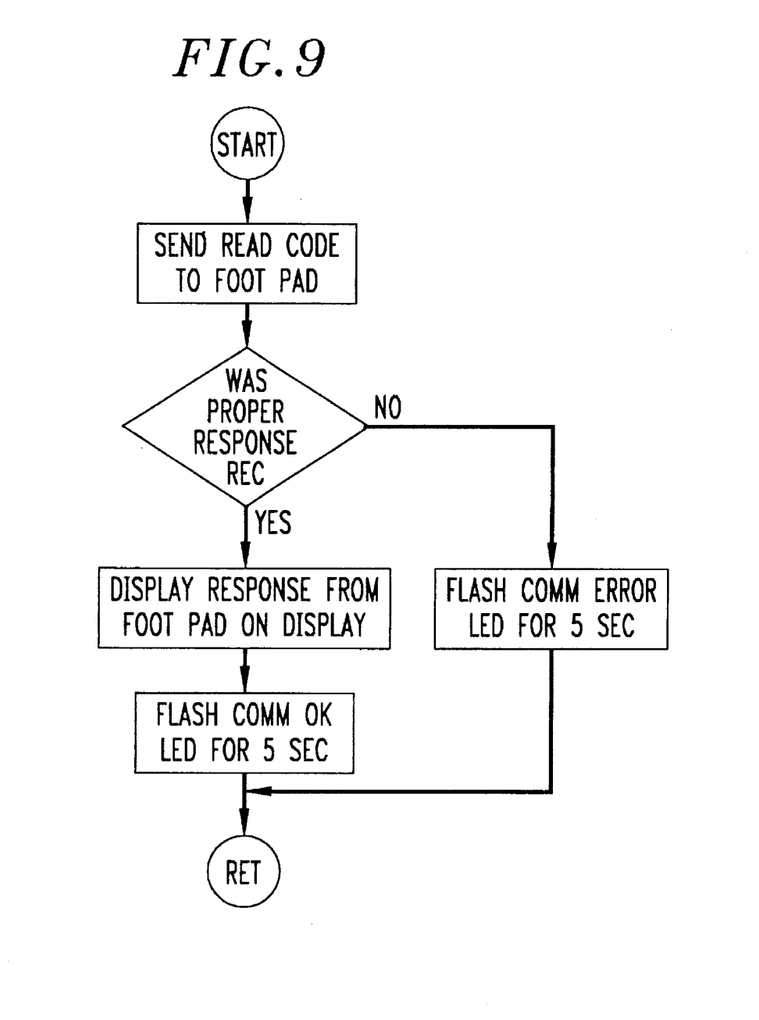
FIG. 9 is a flow chart showing a read routine for the remote unit shown in FIG. 7 to be used in conjunction with the read routine of FIG. 6 to display to a user the value of a set point programmed into the foot-pad.

A read routine activated upon depressing button 55 is shown in FIG. 9. In this routine, the remote sends an encoded code to the food-pad micro-processor. As described above with reference to FIG. 6, the food-pad micro-processor determines if the signal is a proper signal, reads the current set point value, encodes the value and transmits it to the remote unit. The remote unit decodes the received signal, determines if it is a proper signal and then displays the set point in the liquid crystal display. If the signal received from the footpad is not a proper signal, the error light is activated.

Figure 10:
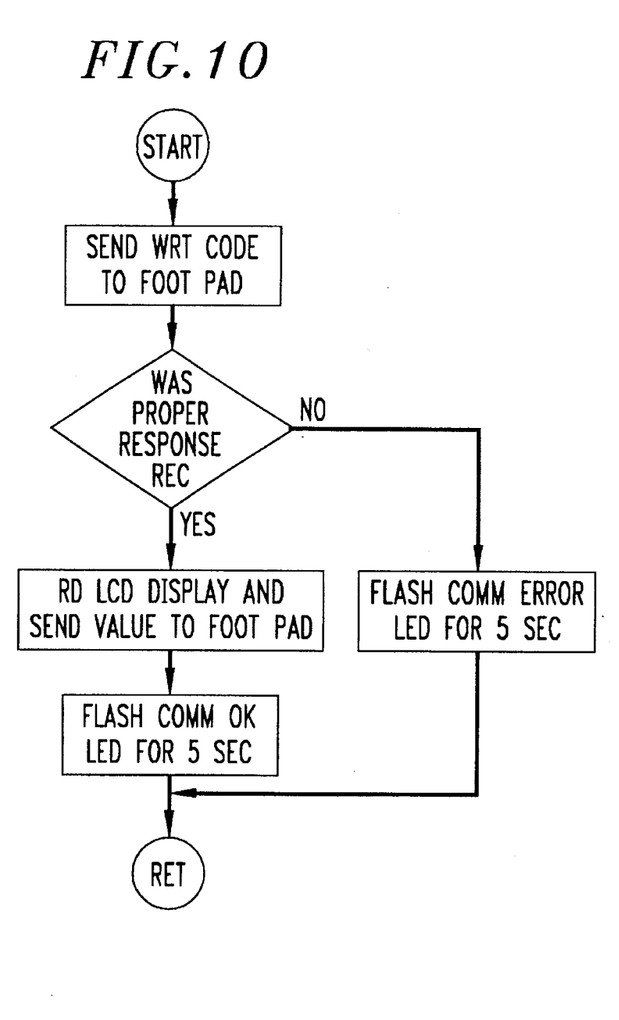
FIG. 10 is a flow chart showing a write routine for the remote unit to be used in conjunction with the write routine of FIG. 6 to program the foot-pad with a new set point.

A write routine that is activated upon depressing transmit button 54 to change the value of the set point in the foot-pad is shown in FIG. 10. In this routine, the remote unit sends an encoded interrupt signal to the foot-pad micro-processor. As described above with reference to FIG. 5, the foot-pad micro-processor receives the signal, decodes it, interrupts the comparator process, and signals the remote that it is ready to receive a new set point value. The remote transmits a new set point value which upon decoding is used to overwrite the previous value. When the new set point value is successfully encoded, the foot-pad micro-processor signals the remote unit of a successful communication and the appropriate indicator light 56 is illuminated. If any of the signals are not successfully received in the expected time, the error light is illuminated and the routine restarts.

The foregoing descriptions have been directed to particular preferred embodiments in accordance with requirements of the patent statutes for purposes of illustration and explanation. As will be apparent to those skilled in the art, many modifications and changes in the devices and procedures set forth above are possible without departing from the scope and spirit of the invention. The following claims as intended to embrace all such modifications and variations.

What is claimed is:

1. A force monitoring system comprising a foot-pad unit and a remote unit wherein the foot-pad unit comprises
a power source,
a tactile force sensor selected from the group consisting of a resistance sensor and a capacitance sensor,
means to translate a force applied to the tactile force sensor to a voltage,
a comparator circuit having a set point and an amplifier that is activated when the voltage from the force sensor is greater than the set point,
a piezo electric annunciator that oscillates at a frequency greater than 22 khz and is driven by the comparator amplifier, and
a housing made of a protecting material encasing the tactile force sensor, the means to translate the force, the comparator circuit, and the piezo electric annunciator; and
the remote unit comprises a receiver matched to the frequency of the piezo-electric annunciator, a convertor, a microprocessor, and a visual display wherein the micro processor is programmed to activate the visual display upon receipt of a signal from the piezo-electric annunciator.

2. The force monitoring system of claim 1 wherein the piezo-electric annunciator also oscillates at a second frequency in the audible range.

3. The force monitoring system of claim 2 further comprising means to secure the foot-pad unit to a shoe.

4. The force monitoring system of claim 1 wherein the foot pad unit further comprises a second piezo-electric annunciator that is driven by the comparator amplifier and oscillates at a frequency in the audible range.

5. A force monitoring system comprising a foot-pad unit and a remote unit wherein the remote unit comprises
a remote unit annunciator that oscillates at a frequency greater than 22 khz,
means to set a new set point, and
a micro-processor programmed to drive the remote unit annunciator to transmit a new set point to the foot-pad unit;
the foot-pad unit comprises
a power source,
a tactile force sensor selected from the group consisting of a resistance sensor and a capacitance sensor,
means to translate a force applied to the tactile force sensor to a voltage,
a foot-pad piezo-electric annunciator driven by the comparator amplifier,
a receiver matched to the frequency of the remote unit annunciator,
means to decode a signal received from the remote unit annunciator,
a comparator circuit having a set point and an amplifier that is activated when the voltage from the force sensor is greater than the set point, the comparator circuit being an analog-to-digital convertor and a micro-processor programmed both to drive the foot pad piezo electric annunciator when the voltage from the tactile force sensor is greater than the set point and to replace the set point when a new set point is received from the remote unit; and
a housing made of a protecting material encasing the tactile force sensor, the means to translate the force, the comparator circuit and the foot-pad piezo electric annunciator; the receiver, and the means to decode.

6. The force monitoring system of claim 5 wherein the foot-pad piezo electric annunciator oscillates at a frequency greater than 22 khz; and the remote unit further comprises a receiver matched to the frequency of the foot pad piezo electric annunciator, a convertor, and a visual display wherein the micro-processor is programmed to activate the visual display upon receipt of a signal from the foot pad piezo electric annunciator.

7. A foot-pad unit comprising:

a power source, a tactile force sensor selected from the group consisting of a resistance sensor and a capacitance sensor, means to translate a force applied to the tactile force sensor to a voltage, a comparator circuit having a set point and an amplifier that is activated when the voltage from the force sensor is greater than the set point, a piezo-electric annunciator driven by the comparator amplifier, and a housing made of a protecting material encasing the tactile force sensor, the means to translate a force, the comparator circuit and the piezo-electric annunciator;

wherein the comparator is an analog voltage comparator having a reference circuit and the set point is the voltage of the reference circuit which comprises at least first and second linearly adjustable pots each of which has a dial extending to an external surface of the housing wherein the first linearly adjustable pot has a dynamic range permitting adjustment of the set point from values of five pounds to five hundred pounds and the second linearly adjustable pot has a dynamic range permitting adjustment of the set point in increments of 1 pound.

8. The foot pad unit of claim 2 further comprising first and second calibration covers each positioned on an external surface of the housing with the first calibration cover surrounding the dial of the first linearly adjustable pot and the second calibration cover surrounding the dial of the second linearly adjustable pot.

9. The foot pad unit of claim 8 further comprising means to secure the foot-pad unit to a shoe.

* * * * *